(12) United States Patent
Zimmermann et al.

(10) Patent No.: US 7,199,241 B1
(45) Date of Patent: *Apr. 3, 2007

(54) PROCESS FOR PREPARING (S) AND (R)-2-[4-(4-CHLOROBENZHYDRYL) PIPERAZIN-1-YL]-ETHOXYACETAMIDE

(75) Inventors: Vincent Zimmermann, Brussels (BE); Emile Cavoy, Ham-sur-Heure (BE); Michel Hamende, Brussels (BE)

(73) Assignee: UCB, S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/250,343

(22) Filed: Oct. 17, 2005

Related U.S. Application Data

(60) Division of application No. 10/920,434, filed on Aug. 18, 2004, now Pat. No. 6,977,301, which is a continuation of application No. 10/441,073, filed on May 20, 2003, now abandoned, which is a continuation-in-part of application No. 10/214,744, filed on Aug. 9, 2002, now abandoned, which is a continuation of application No. 09/865,618, filed on May 29, 2001, now abandoned.

(51) Int. Cl.
C07D 295/145 (2006.01)

(52) U.S. Cl. .................................... 544/396

(58) Field of Classification Search ................ 544/396
See application file for complete search history.

(56) References Cited

U.S. PATENT DOCUMENTS

| | | | |
|---|---|---|---|
| 2,985,589 A | 5/1961 | Broughton et al. | |
| 4,525,358 A | 6/1985 | Baltes et al. | |
| 5,478,941 A | 12/1995 | Cossement et al. | |
| 6,107,492 A | 8/2000 | Futagawa et al. | |
| 6,124,473 A | 9/2000 | Cavoy et al. | |
| 6,977,301 B1 * | 12/2005 | Zimmerman et al. | ....... 544/396 |

FOREIGN PATENT DOCUMENTS

| | | |
|---|---|---|
| EP | 0 157 365 | 1/1985 |
| EP | 0 471 082 | 2/1992 |
| EP | 0 601 028 | 6/1994 |
| EP | 0 617 028 | 9/1994 |
| EP | 0 663828 | 7/1995 |
| EP | 0 687 491 | 12/1995 |
| EP | 0 706 982 | 4/1996 |
| EP | 0 719 749 | 7/1996 |
| EP | 0 801 064 | 10/1997 |
| GB | 2 225 320 | 5/1990 |
| GB | 2 225 321 | 5/1990 |
| WO | 94/06429 | 3/1994 |
| WO | 97/37982 | 10/1997 |

OTHER PUBLICATIONS

Wald et al., Abstr. Pap. Am. Chem. Soc., 219, Part 2, Abstract No. ADPE01A0406 (2000).
Pflum et al., Organic Process Research & Development, vol. 5, No. 2, pp. 110-115 (2001).
Pflum et al., Org. Proc. Res. Dev., ASAP Article10.1021/op0002951 S1083-6160(00)00295-4, Web Release Date: Dec. 8, 2000.
Cavoy et al., Journal of Chromatography A., 769, pp. 49-57 (1997).
Francotte et al., Journal of Chromatography A., 769, pp. 101-107 (1997).
Strube et al., Journal of Chromatography A., 769, pp. 81-92 (1997).

* cited by examiner

*Primary Examiner*—Emily Bernhardt
(74) *Attorney, Agent, or Firm*—Wenderoth, Lind & Ponack, L.L.P.

(57) ABSTRACT

The present invention relates to a process for preparing (S)-2-[4-(4-chlorobenzhydryl)piperazin-1-yl]-ethoxyacetamide and (R)-2-[4-(4-chlorobenzhydryl)piperazin-1-yl]-ethoxyacetamide by separation of a racemic mixture using multiple column chromatography.

13 Claims, No Drawings

PROCESS FOR PREPARING (S) AND (R)-2-[4-(4-CHLOROBENZHYDRYL) PIPERAZIN-1-YL]-ETHOXYACETAMIDE

This is a divisional of Ser. No. 10/920,434, filed Aug. 18, 2004 now U.S. Pat. No. 6,977,301 which is a continuation of Ser. No. 10/441,073, filed May 20, 2003, now abandoned, which is a CIP of Ser. No. 10/214,744, filed Aug. 9, 2002, now abandoned, which is a continuation of Ser. No. 09/865,618, filed May 29, 2001, now abandoned.

The present invention relates to a process for preparing, (S)-2-[4-(4-chlorobenzhydryl)piperazin-1-yl]-ethoxyacetamide and (R)-2-[4-(4-chlorobenzhydryl)piperazin-1-yl]-ethoxyacetamide corresponding to the formulae I and II. (S)-2-[4-(4-chlorobenzhydryl)piperazin-1-yl]-ethoxyacetamide and (R)-2-[4-(4-chlorobenzhydryl)piperazin-1-yl]-ethoxyacetamide are respectively intermediates for the dextrocetirizine and levocetirizine synthesis

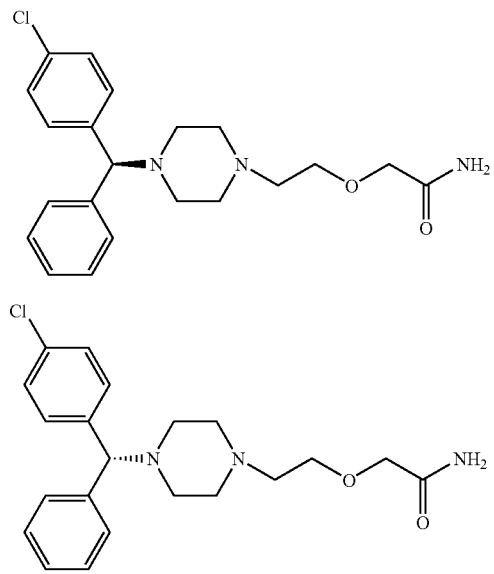

Processes for preparing levocetirizine and dextrocetirizine from its racemic mixture cetirizine ([2-[4-[(4-chlorophenyl)phenylmethyl]-1-piperazinyl]ethoxy]acetic acid) are known from Great Britain patents 2 225 320 and 2 225 321, and from European patent 0 663 828. Processes for preparing cetirizine, an individual optical isomer thereof or a pharmaceutically acceptable salt thereof have been described in European patent 0 058 146, Great Britain patents 2 225 320 and 2 225 321, U.S. Pat. No. 5,478,941, European patent applications 0 601 028 and 0 801 064 and international patent application WO 97/37982. The technique of multiple column chromatography has formed the subject of many publications.

In particular, the technique of simulated mobile bed chromatography has formed the subject of many publications. Mention may be made in particular of U.S. Pat. No. 2,985,589 which describes the operating principle of this technique in detail.

A specific technique of multiple column chromatography known under the name Varicol is described in the international patent application WO 00/25885.

Processes for preparing (S)-2-[4-(4-chlorobenzhydryl) piperazin-1-yl]-ethoxyacetamide and (R)-2-[4-(4-chlorobenzhydryl)piperazin-1-yl]-ethoxyacetamide are known from European patent 0 617 028.

Moreover, European patent 0 471 082 and European patent application 0 719 749 describe the use of the simulated mobile bed chromatographic technique for the separation of racemic mixtures. More particularly, these documents describe the resolution of 1,3-butanediol diacetate and of α-phenylethyl alcohol by means of simulated mobile bed systems comprising 8 or 12 columns filled with chiral stationary phase.

The application of the technique of simulated mobile bed chromatography for the enantiomeric resolution of racemic mixtures has also been described in the article "Lit mobile simulé. Application à la séparation d'isomères optiques [Simulated mobile bed. Application to the separation of optical isomers]" by R. M. Nicoud, Information Chimie No. 368 (May 1995), pp. 113–115. According to this article, the application of the simulated mobile bed technique for the industrial production of optically pure pharmaceutical products is far from being simple: the separations to be carried out are much more difficult and the chromatographic supports are much more expensive than in the case of the existing separations in heavy-tonnage production; in addition, the simulated mobile bed processes adapted to the requirements of production and of quality in the pharmaceutical industry are extremely sensitive to the operation conditions used, in particular the recycling flow rate and the inlet-outlet flow rate.

There was therefore no reason to suppose that the multiple column chromatography technique, in particular the simulated mobile bed technique, the Varicol technique, or the PowerFeed technique, could be used for the application forming the subject of the present invention, and above all that this technique could be transposed to the industrial scale to give, efficiently and with excellent production efficiency, a product having the required purity for a pharmaceutical application.

The present invention therefore relates to a process for preparing (S)-2-[4-(4-chlorobenzhydryl)piperazin-1-yl]-ethoxyacetamide and (R)-2-[4-(4-chlorobenzhydryl)piperazin-1-yl]-ethoxyacetamide, by enantiomeric resolution of racemic 2-[4-(4-chlorobenzhydryl)piperazin-1-yl]-ethoxyacetamide using multiple column chromatography.

Multiple column chromatography (MCC) is a general term for the continuous chromatographic separation technologies (both analytical and preparative) which are based on the continuous controlled injection of (usually binary) mixtures onto a series of linked columns filled with a stationary phase. The separated components of the mixture are then withdrawn continuously from the system. This approach would include, but is not limited to, simulated moving bed chromatography mode (SMB mode), or mode where the inlet and outlet ports are shifted asynchronously (such as the Varicol mode) or mode in which inlet and oulet flowrates and/or concentrations are changing in time during the switching period.

The Varicol system is described in the international patent application WO 00/25885, which is incorporated by reference.

The mode in which fluid flowrates are changing in time during the switching period is described in U.S. Pat. No. 5,102,553, which is incorporated by reference.

In another embodiment, the present invention therefore relates to a process for preparing (S)-2-[4-(4-chlorobenzhydryl)piperazin-1-yl]-ethoxyacetamide and (R)-2-[4-(4-chlorobenzhydryl)piperazin-1-yl]-ethoxyacetamide, by enantiomeric resolution of racemic 2-[4-(4-chlorobenzhydryl)piperazin-1-yl]-ethoxyacetamide using simulated mobile bed chromatography.

A simulated mobile bed (SMB) consists of a series of fixed-bed columns connected in series. The charge (solution to be separated) and the eluent are injected continuously into the system while the purified compounds are removed continuously in the extract (compound most strongly retained) and the raffinate (compound least strongly retained). The points of injection and of removal are shifted synchronously in the direction of flow of the mobile phase at constant time intervals, thus simulating a counter-current flow of solid and of liquid. A switching time (or period) is the interval of time which separates two shifts of the points of injection and of removal. A cycle consists of successive periods such that the points of injection and of removal regain their initial positions.

Four zones are defined in a simulated mobile bed, these being delimited by the inlet/outlet points according to:

| zone I: | between the eluent and extract points; |
|---|---|
| zone II: | between the extract and charge points; |
| zone III: | between the charge and raffinate points; |
| zone IV: | between the raffinate and eluent points. |

Two injection points and two removal points are thus distinguished, which are always arranged between two zones, it being understood that one zone can contain several columns. In the process according to the invention, a variable number of columns can be used. The simulated mobile bed system must contain a minimum of three columns. In one embodiment of the invention, the simulated mobile bed consists of six columns, of which, in each case, one is in zones I and IV and, in each case, two are in zones II and III. In another embodiment of the invention, two simulated mobile bed systems are used, each containing six columns, these two systems being placed in series, which brings the number of columns used to a total number of twelve. This operating mode makes it possible to carry out the optical resolution of the racemic mixture by passage through the first simulated mobile bed system, and then to further purify the raffinate or the extract by passage through the second simulated mobile bed system. According to this specific embodiment, it may prove to be useful to make use of an intermediate step of concentrating between the passage through the first simulated mobile bed and the passage through the second simulated mobile bed.

It has been noted, surprisingly, that the process according to the present invention makes it possible to obtain, in an industrial plant, (S) and (R)-2-[4-(4-chlorobenzhydryl)piperazin-1-yl]-ethoxyacetamide with a very high production efficiency, which can be up to 1030 g of racemic separated per kg of chiral stationary phase and per day and a low volume of consumed and recycled solvent (348 liter/kg of racemic separated). In one embodiment of the invention, the simulated mobile bed consists of eight columns.

As regards the size of the columns, this can vary within a wide range as a function of the desired production efficiency. Preferably, short columns (from 5 to 50 cm) are used, preferably less than or equal to 10 cm in length.

Different configurations can be used for synchronously shifting of the injection and removal points. For example, electrostatic or pneumatic valves prove to be suitable for this purpose. The columns are filled with chiral stationary phase. The chiral stationary phases which can be used according to the present invention can be chosen from phases based on silica gel supporting polymeric compounds such as polysaccharide derivatives (such as esters and carbamates of cellulose or of amylose), polyacrylic derivatives and polyamide derivatives. Examples of phases which can be used according to the invention are the phases Chiralcel (OD,OJ) and Chiralpak (AD, AS) (available from Daicel Chemical Industries), Chirobiotic V and Cyclobond I 2000 SN (available from Advanced Separation Technologies Inc.), Kromasil CHI 1 (available from EKA Nobel), ULTRON ES-OVM (available from Rockland Technologies, Inc.) and celluspher OJ (available from Merck). These chiral stationary phases consist of particles whose size can range between 5 and 300 µm, preferably from about 10 to 20 µm.

According to one embodiment of the invention, the simulated moving bed chromatographic system uses at least one column packed with an optical resolution packing material, said packing material consisting of silica gel supporting amylose tris(3,5-dimethylphenylcarbamate) or a chemically modified form thereof. Preferably, the average particle diameter of the packing material is 1 to 300 µm. Preferably, the particles of the packing material are porous; and in particular, the pore diameter of the particles is 10 Å–5000 Å. Preferably, the amylose tris(3,5-dimethylphenylcarbamate) or chemically modified form thereof is 1 to 99% weight percent of the silica gel support.

The eluent which can be used can be varied in natures.

Generally, the multiple column system uses an eluent an alcohol or mixture of alcohol and of alkane in a proportion (by volume) of between 5/95 and 100/0.

Preferably, an alcohol or mixture of alcohol and of alkane in a proportion (by volume) of between 50/50 and 100/0 will be chosen. The best results have been obtained when the simulated mobile bed system uses an eluent selected from methanol, or a mixture of n-heptane and n-propanol.

According to one preferred embodiment of the process according to the present invention, a recycling pump for ensuring the internal circulation of the fluid is placed between the last and the first column. The presence of this recycling pump not only makes it possible to avoid the risk of pollution of the eluent, but also to minimize the storage problems.

The process of the invention is performed at a temperature of 5 to 50° C.

According to another embodiment, the present invention relates to a process for preparing (S)-[2-[4-[(4-chlorophenyl)phenylmethyl]-1-piperazinyl]ethoxy]acetic acid, (R)-[2-[4-[(4-chlorophenyl)phenylmethyl]-1-piperazinyl]ethoxy]acetic acid) and the pharmaceutically acceptable salts thereof from hydrolysis of respectively (S)-2-[4-(4-chlorobenzhydryl)piperazin-1-yl]-ethoxyacetamide and (R)-2-[4-(4-chlorobenzhydryl)piperazin-1-yl]-ethoxyacetamide, the enantiomeric resolution of the racemic mixture of 2-[4-(4-chlorobenzhydryl)piperazin-1-yl]-ethoxyacetamide being carried out by multiple column chromatography.

According to another embodiment, the present invention relates to a process for preparing (S)-[2-[4-[(4-chlorophenyl)phenylmethyl]-1-piperazinyl]ethoxy]acetic acid, (R)-[2-[4-[(4-chlorophenyl)phenylmethyl]-1-piperazinyl]ethoxy]acetic acid) and the pharmaceutically acceptable salts thereof from hydrolysis of respectively (S)-2-[4-(4-chlorobenzhydryl)piperazin-1-yl]-ethoxyacetamide and (R)-2-[4-(4-chlorobenzhydryl)piperazin-1-yl]-ethoxyacetamide, the enantiomeric resolution of the racemic mixture of 2-[4-(4-chlorobenzhydryl)piperazin-1-yl]-ethoxyacetamide being carried out by simulated mobile bed chromatography. (S)-[2-[4-[(4-chlorophenyl)phenylmethyl]-1-piperazinyl]

ethoxy]acetic acid is generated by the hydrolysis in acidic medium of (S)-2-[4-(4-chlorobenzhydryl)piperazin-1-yl]-ethoxyacetamide. (R)-[2-[4-[(4-chlorophenyl)phenylmethyl]-1-piperazinyl]ethoxy]acetic acid is generated by the hydrolysis in acidic medium of (R)-2-[4-(4-chlorobenzhydryl)piperazin-1-yl]-ethoxyacetamide.

The present invention relates to a process for preparing (S)-[2-[4-[(4-chlorophenyl)phenylmethyl]-1-piperazinyl]ethoxy]acetic acid dihydrochloride (dextrocetirizine dyhydrochloride) from (S)-[2-[4-[(4-chlorophenyl)phenylmethyl]-1-piperazinyl]ethoxy]acetamide.

The present invention relates to a process for preparing (R)-[2-[4-[(4-chlorophenyl)phenylmethyl]-1-piperazinyl]ethoxy]acetic acid dihydrochloride (levocetirizine dyhydrochloride) from (R)-[2-[4-[(4-chlorophenyl)phenylmethyl]-1-piperazinyl]ethoxy]acetamide.

The examples which follow illustrate the process according to the present invention and show operating details with reference to preferred embodiments of the invention, it being clearly understood that the invention is not limited to these specific operating conditions.

EXAMPLE 1

Production Efficiency on the Pilot Industrial Scale

In this example, the enantiomeric resolution of racemic 2-[4-(4-chlorobenzhydryl)piperazin-1-yl]-ethoxyacetamide is carried out on a Licosep 8-200 system, available from Novasep (France). This system comprises one eight-column simulated mobile bed system in which the eight columns have a diameter of 20.2 cm and are individually packed with 1600 g of Chiralpak AS phase available from Daicel Chemical Industries. The eluent used is methanol. Each zone contains two columns. The total concentration of the charge is 50 g/l, the switching time is 4.6 min and the pressure is 15 bar. The flow rates are 230 l/h for zone I, 4.6 l/h for the charge; 170 l/h for the eluent; 158.1 l/h for the extract and 16.5 l/h for the raffinate.

The yields and purities obtained for each enantiomer of 2-[4-(4-chlorobenzhydryl)piperazin-1-yl]-ethoxyacetamide are summarized in Table 1.

TABLE 1

|  | Extract | Raffinate |
| --- | --- | --- |
| Total Concentration (g/l) | 0.68 | 7.4 |
| Purity (%) | 99.6 | 93.8 |

(R)-2-[4-(4-chlorobenzhydryl)piperazin-1-yl]-ethoxyacetamide is in the extract and (S)-2-[4-(4-chlorobenzhydryl)piperazin-1-yl]-ethoxyacetamide is in the raffinate.

In this example the productivity expressed in g of racemic/kg of chiral stationary phase/day is 430 g/kg/day and the solvent consumption is 758 liter/kg of racemic separated.

The parameter k' is 3.8 at 30° C.

By varying the separation conditions, the productivity can be increased and the solvent consumption diminished.

EXAMPLE 2

Production Efficiency on the Pilot Industrial Scale

In this example, the enantiomeric resolution of racemic 2-[4-(4-chlorobenzhydryl)piperazin-1-yl]-ethoxyacetamide is carried out on a Licosep 8-200 system, available from Novasep (France). This system comprises one eight-column simulated mobile bed system in which the eight columns have a diameter of 20.2 cm and are individually packed with 1400 g of Chiralpak AD phase available from Daicel Chemical Industries. The eluent used is a 50/50 v/v n-heptane/n-propanol mixture.

Zone I and IV contain one column whilst zone II and III respectively comprise four and two columns. The total concentration of the charge is 40 g/l, the switching time is 0.79 min and the pressure is 40 bar. The flow rates ranges are 393.1–410 l/h for zone I, 11.5–12.5 l/h for the charge; 160–177 l/h for the eluent; 112–133 l/h for the extract and 48.5–60 l/h for the raffinate. The raffinate and the extract leave the simulated mobile bed, having been diluted and are preconcentrated on falling-film evaporators. The distilled solvents are recycled.

The yields and purities obtained for each enantiomer of 2-[4-(4-chlorobenzhydryl)piperazin-1-yl]-ethoxyacetamide are summarized in Table 2.

TABLE 2

|  | Extract | Raffinate |
| --- | --- | --- |
| Total Concentration (g/l) | 1.6 | 5.6 |
| Purity (%) | 99.1 | 87.5 |

(R)-2-[4-(4-chlorobenzhydryl)piperazin-1-yl]-ethoxyacetamide is in the extract and (S)-2-[4-(4-chlorobenzhydryl)piperazin-1-yl]-ethoxyacetamide is in the raffinate.

In this example the productivity expressed in g of racemic/kg of chiral Stationary phase/day is 1030 g/kg/day and the solvent consumption is 358 liter/kg of racemic separated.

The parameter k' is 1.06 at 40° C.

By varying the separation conditions, the raffinate purity can be increased.

EXAMPLE 3

Production Efficiency on the Pilot Industrial Scale

In this example, the enantiomeric resolution of racemic 2-[4-(4-chlorobenzhydryl)piperazin-1-yl]-ethoxyacetamide is carried out on a Licosep 8-200 system, available from Novasep (France). This system comprises one eight-column simulated mobile bed system in which the eight columns have a diameter of 20.2 cm and are individually packed with 1800 g of Chiralpak AD phase available from Daicel Chemical Industries. The eluent used is a 50/50 v/v n-heptane/n-propanol mixture.

Zone I and IV contain one column whilst zone II and III respectively comprise four and two columns. The total concentration of the charge is 40 g/l, the switching time is 1.06–1.4 min (1.12 min) and the pressure is 40 bar. The flow rates ranges are 278–348 l/h (347 l/h) for zone I, 9.5–12.5 l/h (12 l/h) for the charge; 124–155 (155 l/h) for the eluent; 101.9–141 l/h (131 l/h) for the extract and 26–57 l/h (36 l/h) for the raffinate.

The raffinate and the extract leave the simulated mobile bed, having been diluted and are preconcentrated on falling-film evaporators. The distilled solvents are recycled.

The yields and purities obtained for each enantiomer of 2-[4-(4-chlorobenzhydryl)piperazin-1-yl]-ethoxyacetamide are summarized in Table 3.

TABLE 3

|  | Extract | Raffinate |
|---|---|---|
| Total Concentration (g/l) | 1.9 | 7.1 |
| Purity (%) | 99.2 | 98.1 |

(R)-2-[4-(4-chlorobenzhydryl)piperazin-1-yl]-ethoxyacetamide is in the extract and (S)-2-[4-(4-chlorobenzhydryl)piperazin-1-yl]-ethoxyacetamide is in the raffinate.

In this example the productivity expressed in g of racemic/kg of chiral Stationary phase/day is 795 g/kg/day and the solvent to recover is 348 liters/kg of racemic separated.

The material balance by mass for this pilot study is very satisfactory: for 2258 kg of racemic mixture consumed, the recovery of the desired enantiomer was 44,2% (50% being the maximum achievable)

The parameter k' is 1.06 at 40° C.

EXAMPLE 4

Production Efficiency on the Industrial Scale

In this example, the enantiomeric resolution of racemic 2-[4-(4-chlorobenzhydryl)piperazin-1-yl]-ethoxyacetamide is carried out on a Licosep 8-350 system, available from UCB Farchim (Switzerland). This system comprises one eight-column simulated mobile bed system in which the eight columns have a diameter of 35.0 cm and are individually packed with 4160 g of Chiralpak AD phase available from Daicel Chemical Industries. The eluent used is a 50/50±2 v/v n-heptane/n-propanol mixture.

Zone I and IV contain one column whilst zone II and III respectively comprise four and two columns. The total concentration of the charge is 40±2 g/l, the switching time is 1.0–1.24 min (1.19 min) and the pressure is 40 bar. The flow rates ranges are 494–680 l/h (635 l/h) for zone II, 34–43 l/h (37 l/h) for the charge; 460–575 l/h (473 l/h) for the eluent; 378–474 l/h (381 l/h) for the extract and 115–145 l/h (129 l/h) for the raffinate.

The raffinate and the extract leave the simulated mobile bed, having been diluted and are preconcentrated on falling-film evaporators. The distilled solvents are recycled.

The yields and purities obtained for each enantiomer of 2-[4-(4-chlorobenzhydryl)piperazin-1-yl]-ethoxyacetamide are summarized in Table 4.

TABLE 4

|  | Extract | Raffinate |
|---|---|---|
| Total Concentration (g/l) | 2.0 | 5.6 |
| Purity (%) | 99.0 | 98.9 |

(R)-2-[4-(4-chlorobenzhydryl)piperazin-1-yl]-ethoxyacetamide is in the extract and (S)-2-[4-(4-chlorobenzhydryl)piperazin-1-yl]-ethoxyacetamide is in the raffinate.

In this example the productivity expressed in g of racemic/kg of chiral Stationary phase/day is 852.7 g/kg/day. The parameter k' is 1.06 at 40° C.

The material balance by mass for this industrial scale is very satisfactory: for 606 kg of racemic mixture consumed, the recovery of the wanted enantiomer was 45.8% (50% being the maximum achievable).

EXAMPLE 5

Process for Preparing (R)-[2-[4-[(4-chlorophenyl)phenylmethyl]-1-piperazinyl]ethoxy]acetic Acid Dihydrochloride Crude (R)-2-[4-(4-chlorobenzhydryl)piperazin-1-yl]-ethoxyacetamide, as obtained above, is isolated by evaporation under reduced pressure of a n-propanol/n-heptane solution (concentrated extract). The concentrated extract is evaporated under vacuum to remove solvent whilst maintaining the temperature of the contents below 40° C.

The product then crystallises and the suspension is further evaporated at 40° C., following by drying at 45° C. with a final vacuum of less than 30 mbar.

The product is dissolved in isopropyl alcohol (0.4 volume) and diisopropylether (7.6 volume) by heating to reflux temperature (65° C.) for at least 30 minutes.

The hot solution is then clarified using a closed filter and the filtrate is transferred to a crystallisation vessel.

The clarified solution is then cooled down to approximately 0° C. and the resulting suspension is centrifuged in order to isolate the product.

The product is dried under vacuum (45° C.) with a final pressure less than 30 mbar.

Water (1 volume) and a concentrated aqueous solution of hydrogen chloride (HCl, 1 volume) are respectively added to the re-crystallised (R)-2-[4-(4-chlorobenzhydryl)piperazin-1-yl]-ethoxyacetamide. The mixture is heated up to 65° C. for at least 4 hours.

The reaction mixture is neutralized with a concentrated aqueous solution of sodium hydroxide (approximately 50% NaOH) to reach a pH value of 4.5–5.0.

Toluene (10 volumes) is then added while stirring to the reactor contents. Water is removed by azeotropic distillation (water/toluene) under reduced pressure below 70° C.

The hot toluene suspension is filtrated. The filtrate is evaporated under vacuum to remove toluene (between 50 and 65° C., final pressure less than 30 mbar), and the residue is then transferred to a cristallisation vessel with acetone (4 volumes) and process water (0.2 volume). A solution of hydrochloric acid (2.1 equivalents of HCL) in acetone is then added to the acetone solution previously obtained in the crystallisation vessel.

This mixture is heated up to reflux (55° C.) before being cooled down to approximately 0° C. for the crystallisation.

The suspension is centrifuged and the filter cake is washed with acetone (0.5 volume).

The final product is dried under vacuum (75° C.) with a final pressure less than 30 mbar. (R)-[2-[4-[(4-chlorophenyl)phenylmethyl]-1-piperazinyl]ethoxy]acetic acid dihydrochloride (levocetirizine dihydrochloride) is obtained.

EXAMPLE 6

Process for Preparing (S)-[2-[4-[(4-chlorophenyl)phenylmethyl]-1-piperazinyl]ethoxy]acetic Acid Dihydrochloride Crude (S)-2-[4-(4-chlorobenzhydryl)piperazin-1-yl]-ethoxyacetamide, as obtained above, is isolated by evaporation under reduced pressure of a n-propanol/n-heptane solution (concentrated raffinate).

A process as described in example 5 is applied with the concentrated raffinate in place of the concentrated extract.

(S)-[2-[4-[(4-chlorophenyl)phenylmethyl]-1-piperazinyl]ethoxy]acetic acid dihydrochloride (dextrocetirizine dihydrochloride) is obtained.

EXAMPLE 7

Production Efficiency by SMB on the Pilot Industrial Scale

In this example, the enantiomeric resolution of racemic 2-[4-(4-chlorobenzhydryl)piperazin-1-yl]-ethoxyacetamide is carried out on a Licosep 8-200 system, available from Novasep (France). This system comprises one eight-column simulated mobile bed system in which the eight columns have a diameter of 20.2 cm and are individually packed with 1400 g of Chiralpak AD phase available from Daicel Chemical Industries. The eluent used is a 50/50 v/v n-heptane/n-propanol mixture.

Zone I and IV contain one column whilst zone II and III respectively comprise four and two columns. The total concentration of the charge is 40 g/l, the switching time is 0.824 min and the pressure is 20 bar. The flow rates are 436.49 l/h for zone I, 23.75 l/h for the charge; 262.95 l/h for the eluent; 196.83 l/h for the extract and 89.87 l/h for the raffinate.

The yields and purities obtained for each enantiomer of 2-[4-(4-chlorobenzhydryl)piperazin-1-yl]-ethoxyacetamide are summarized in the table 5.

TABLE 5

|  | Extract | Raffinate |
| --- | --- | --- |
| Total Concentration (g/l) | 2.284 | 5.231 |
| Purity (%) | 98.89 | 94.83 |

(R)-2-[4-(4-chlorobenzhydryl)piperazin-1-yl]-ethoxyacetamide is in the extract and (S)-2-[4-(4-chlorobenzhydryl)piperazin-1-yl]-ethoxyacetamide is in the raffinate.

In this example the productivity expressed in g of racemic/kg of chiral Stationary phase/day is 2035 g/kg/day and the solvent consumption is 301.8 liter/kg of racemic separated.

The parameter k' is 1.405 at 30° C.

EXAMPLE 8

Production Efficiency by VARICOL Simulation on the Pilot Industrial Scale

In this example, the enantiomeric resolution of racemic 2-[4-(4-chlorobenzhydryl)piperazin-1-yl]-ethoxyacetamide is supposed to be carried out on a Licosep 8-200 system, available from Novasep (France). This system comprises one eight-column multiple column chromatographic system, seven columns of 20.2 cm of diameter are connected and are individually packed with 1400 g of Chiralpak AD phase available from Daicel Chemical Industries. The eluent used is a 50/50 v/v n-heptane/n-propanol mixture.

Zone I contain 1.05 column Zone II contain 3.2 columns, Zone III contain 1.8 column and Zone IV contain 0.95 column. The total concentration of the charge is 40 g/l, the switching time is 0.749 min and the pressure is 20 bar. The flow rates are 487.86 l/h for zone I, 22.537 l/h for the charge; 300.32 l/h for the eluent; 214.9 l/h for the extract and 107.95 l/h for the raffinate.

The yields and purities obtained for each enantiomer of 2-[4-(4-chlorobenzhydryl)piperazin-1-yl]-ethoxyacetamide are summarized in the table 6.

TABLE 6

|  | Extract | Raffinate |
| --- | --- | --- |
| Total Concentration (g/l) | 1.988 | 4.134 |
| Purity (%) | 98.92 | 94.95 |

(R)-2-[4-(4-chlorobenzhydryl)piperazin-1-yl]-ethoxyacetamide is in the extract and (S)-2-[4-(4-chlorobenzhydryl)piperazin-1-yl]-ethoxyacetamide is in the raffinate.

In this example the productivity expressed in g of racemic/kg of chiral Stationary phase/day is 2207.7 g/kg/day and the solvent consumption is 358.1 liter/kg of racemic separated.

The parameter k' is 1.405 at 30° C.

8.5% increase in productivity, 18.65% increase in solvent consumption but with 7 columns instead of 8 columns (8.7% economy in CSP and column cost)

The invention claimed is:

1. Chromatographic process for preparing (S)-2-[4-(4-chlorobenzhydryl)piperazin-1-yl]-ethoxyacetamide and (R)-2-[4-(4-chlorobenzhydryl)piperazin-1-yl]-ethoxyacetamide, by enantiomeric resolution of 2-[4-(4-chlorobenzhydryl)piperazin-1-yl]-ethoxyacetamide, which process comprises using a system comprising series of fixed-bed columns connected in series, wherein the charge (solution of the compounds to be separated) and the eluent are injected continuously into the system while the separated compounds are removed continuously in the extract (compound most strongly retained) and the raffinate (compound least strongly retained), wherein the system comprises at least six columns filled with chiral stationary phase.

2. Process according to claim 1, wherein the chiral stationary phase is chosen from phases based on silica gel supporting polymeric compounds.

3. Process according to claim 1, wherein the chiral stationary phase is a phase based on silica gel supporting an ester or a carbamate of cellulose or of amylose.

4. Process according to claim 1, wherein the system uses at least one column packed with an optical resolution packing material, said packing material consisting of silica gel supporting amylose tris(3,5-dimethylphenylcarbamate) or a chemically modified form thereof.

5. Process according to claim 4, wherein the average particle diameter of the packing material is 1 to 300 μm.

6. Process according to claim 5 wherein the particles of the packing material are porous.

7. Process according to claim 6, wherein the pore diameter of the particles is 10 Å–5000 Å.

8. Process according to claim 4, wherein the amylose tris(3,5-dimethylphenylcarbamate) or chemically modified form thereof is 1 to 99% weight percent of the silica gel support.

9. Process according to claim 1, wherein it is performed at a temperature of 5–50° C.

10. Process according to claim 1, wherein the system comprises eight columns.

11. Process according to claim 1, wherein the system uses an eluent an alcohol or mixture of alcohol and of alkane in a proportion (by volume) of between 50/50 and 100/0.

12. Process according to claim 1, wherein the system uses an eluent selected from methanol, or a mixture of n-heptane and n-propanol.

13. Process according to claim 2, wherein the polymeric compounds are selected from polysaccharide derivatives, polyacrylic derivatives and polyamide derivatives.

* * * * *